US00PP09093P

United States Patent [19]

Flemer, III

[11] Patent Number: Plant 9,093

[45] Date of Patent: Mar. 28, 1995

[54] *QUERCUS PALUSTRIS* 'PRINGREEN'

[75] Inventor: William Flemer, III, Princeton, N.J.

[73] Assignee: Newplant Associates, Princeton, N.J.

[21] Appl. No.: 176,889

[22] Filed: Jan. 3, 1994

[51] Int. Cl.[6] ..... A01H 5/00
[52] U.S. Cl. ..... Plt./53.7
[58] Field of Search ..... Plt. 53.7

*Primary Examiner*—James R. Feyrer
*Attorney, Agent, or Firm*—Frank B. Robb

[57] ABSTRACT

A *Quercus palustris* newly found seedling which has developed into an unusual, very upright, narrow, fastigiate tree, not heretofore noted in the pin oak family, with very dense branches having glossy dark green leaves.

1 Drawing Sheet

BACKGROUND OF THE INVENTION

This invention relates to a *Quercus palustris* seedling discovered and noted for its very narrow dense crown, discovered by me during the course of intense observation in the growing and selecting of trees having different new characteristics, in a nursery near South Brunswick, N.J.

We plant and grow for the market many different varieties of trees and are constantly on the lookout for trees and other plants which appear to have attractive characteristics of one kind or another for sale and further development.

I am constantly observing any plants and particularly trees, which appear to have different characteristics from their parents, and thus when the seedling described herein, appeared from a mass planting of *Quercus palustris* seedlings grown from seed harvested from *Quercus palustris* 'Crownright' which had been planted to provide a selection of improved trees in a row of pin oaks, I felt that it was worthwhile to propagate it and determine its potential.

The unusually upright, narrow shape of this seedling which were initially observed, upon closer inspection was found to be a stable characteristic, and successive reproduction by bud grafting on *Quercus palustris* seedlings. established that the attractive form came true in successive propagation, producing the identical fastigiate branching habit and crown of the seed parent tree.

For identification purposes, I have chosen to designate this new tree as 'Pringreen' for commerical purposes.

I have caused the asexual reproduction of my new tree by bud grafting on the property of Princeton Nurseries in South Brunswick Township, N.J. as before stated and found in all cases that the characteristics set forth are repeated in successive generations. The understock plants were seedlings of *Quercus palustris*. As far as I am aware there is no other known fastigiate native American oak.

In order to illustrate the before described characteristics, I have caused the trees to be shown by photographic means and the drawing appended hereto does in fact disclose those heretofore stated as nearly as possible by such means.

As a basis for color references I have used the Munsell Color Fan as published by Munsell Color Company, where color references are in my judgment of importance, or helpful to described the plant.

Since the outline and branching habit with fastigiate crown of glossy, dark green leaves are the outstanding features the color is somewhat less emphasized but still notable as a distinct aspect.

Details of the tree as far as possible to assemble are set forth in the following specific summary, and in the claim appended hereto.

Parentage:
- *Seed parent.*—*Quercus palustris* 'Crownright' (U.S. Plant Pat. No. 2,936, now expired).
- *Pollen parent.*—Not known. Newly found seedling of *Quercus palustris* 'Crownright'.

Tree: Medium size. The shape of the tree is very narrow, upright columnar crown. The young tree forms a central leader, and is more terminally dominant than other *Quercus palustris* trees. Very upright — fastigiate. Tall. Hardy.

Trunk: Slender, smooth.

Branches: Slender, smooth.
- *Color.*—Grayish olive green-Munsell Color Chart 5GY3/2.
- *Lenticels.*—Abundant, very small. Number — 15 to 17 per cm of twig length.

Leaves:
- *Quantity.*—Abundant, dense.
- *Length.*—16 to 18 cm.
- *Width.*—11 to 13 cm.
- *Shape.*—Pinnate with 7 lobes, sinuses 4 to 5 cm deep. Cuneate at the base.
- *Color.*—Upper surface-dark yellowish green 10GY 4/5. Fall coloration of trees is dark red 2.5R 3/7. Leaves are thick with glossy upper surfaces and small axillary tufts of hair on the lower surfaces. They are retained on the tree into the winter and are shed gradually over a period from mid-December through mid February. Leaf retention does not differ from that of the species.
- *Margin.*—Crenate — smooth edge-sinuately pinnatified with 7 oblong dentate lobes.
- *Petiole.*—Short.
- *Glands.*—None.

Flowers: Not significant, inconspicuous slender catkin.

Petalage: None.

Fruits: None observed.

In summary it may be noted that this tree is not an interspecific hybrid and its leaves and dormant buds exhibit the shape and size of typical *Quercus palustris* leaves and buds.

The tree has not been grown in sweet soils and would not be expected to differ markedly from typical *Quercus palustris* trees, except as indicated.

It has not yet flowered or borne acorns and will not do so for many years. Thus the date of flowering and time of acorn release have not been determined, but it is anticipated that they would differ markedly from typical *Quercus palustris* trees.

I claim:

1. A *Quercus palustris* tree of the class described and disclosed herein, characterized particularly as to novelty by the narrow, dense, fastigiate crown of glossy dark green leaves which distinguish the tree from other known American oak trees.

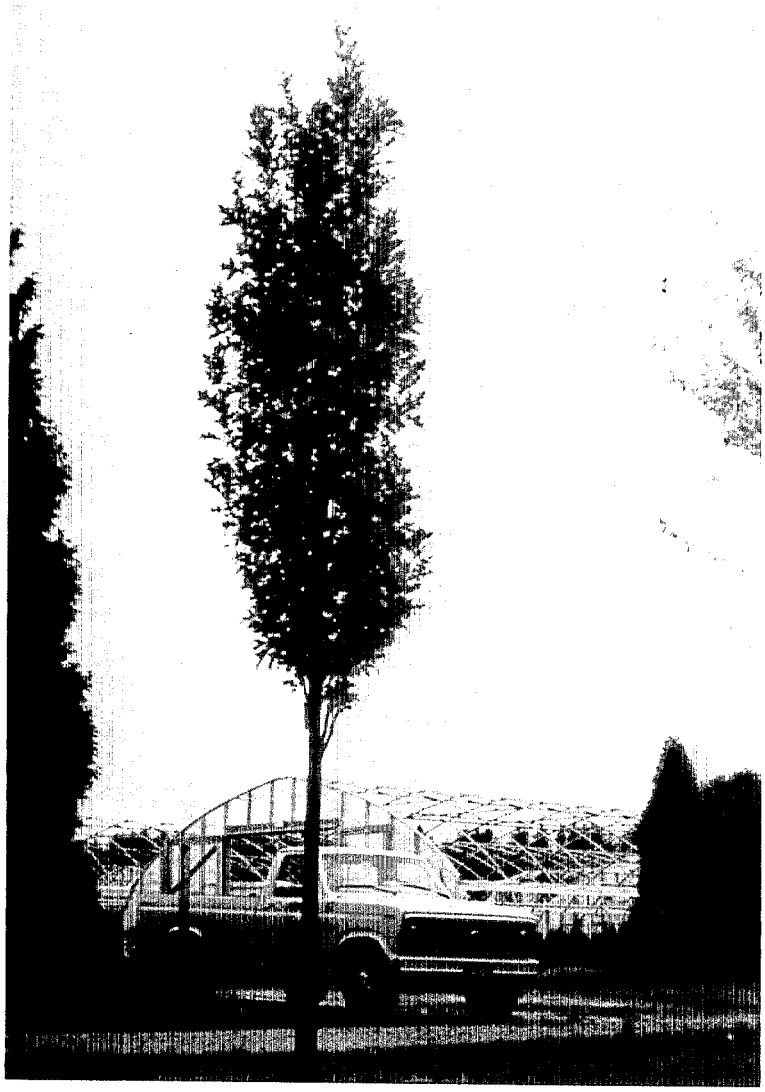

* * * * *